United States Patent [19]

Royston et al.

[11] Patent Number: 4,675,386

[45] Date of Patent: Jun. 23, 1987

[54] MONOCLONAL ANTIBODY METHODS AND COMPOSITIONS SPECIFIC FOR SINGLE ANTIGENS IN ANTIGEN AGGREGATES

[75] Inventors: Ivor Royston; John Majda, both of LaJolla; Gayle Yamamoto, San Diego, all of Calif.

[73] Assignee: Regents of the University of California, Berkeley, Calif.

[21] Appl. No.: 495,728

[22] Filed: May 19, 1983

Related U.S. Application Data

[63] Continuation of Ser. No. 97,777, Nov. 27, 1979, abandoned.

[51] Int. Cl.$^4$ .................. A61K 39/395; C12P 21/00; C12N 15/00; C12N 5/00
[52] U.S. Cl. .................................. 530/387; 530/808; 435/68; 435/172.2; 435/240; 435/948; 436/548; 424/85
[58] Field of Search .................... 424/13, 85, 86, 87, 424/88, 89, 92; 435/172, 68, 172.2, 240, 948; 260/112 R, 112 B; 935/90, 92, 103; 436/548; 530/387, 808

[56] References Cited

U.S. PATENT DOCUMENTS 4,223,005  9/1980  Teodorescu .......................... 424/12
4,284,412  8/1981  Hansen .............................. 424/12 X

OTHER PUBLICATIONS

Lampson, J. of Supramol. Structure, vol. 6, No. 3, 1977, pp. 441–448.
Kennett, Terminal Progress Report, CA-18930, US Dept. HEW (now HHS) Nat. Cancer Inst., Bethesda, Md., 3 pp. Tables 1–7, FIGS. 1, 2a, 2b.
White, J. Exp. Med., vol. 148, Sep. 1, 1978, pp. 664–673.
Williams, Cell, vol. 12, 1977, pp. 663–670, 672, 673.
McMichael, Eur. J. Immunol., vol. 9, 1979, pp. 205–210.
Barnstable, Cell, vol. 14, May 1978, pp. 9–20.
Melchers, (Ed.) Lymph, Hybridomas, 2nd Workshop on Functional Properties of Tumors of T & B Lymph, Springer Verlag, Berlin/N.Y., 1978, pp. IX–XVIII.
Trucco, supra, pp. 66–69.
Levy, supra, pp. 164–169.
Fox, C & EN, Jan. 1, 1979, pp. 15–17.
Kohler & Milstein, Nature, vol. 256, p. 975, pp. 495–497.
Parham & Bodmer, Nature, vol. 276, 1978, pp. 397–399.
Smith, J. Immunol., vol. 110, 1973, pp. 884–887.
Williams, J. Clin. Invst., vol. 52, 1973, pp. 283–295.
Bobrobe, J. Immunol., vol. 112, 1974, pp. 520–527.
Kung, Science, vol. 206, Oct. 19, 1979, pp. 347–349.
Reinherz, Proc. Natl. Acad. Sci. USA, vol. 76, Aug. 1979, pp. 4061–4065.
Reinherz, J. of Immunol., vol. 123, Sep. 1979, pp. 1311–1317.
Kennett, SSIE Data Bank, abstract of grant 5/77–4/79, Ab. No. ICA 189303.
Herzenberg et al., SSIE Data Bank, abstract of grant 9/77–7/79, Ab. No. ICA 468120.
Bach, *Immunology*, Wiley & Sons, N.Y., 1982, pp. 76–77.

*Primary Examiner*—Esther M. Kepplinger
*Attorney, Agent, or Firm*—Bertram I. Rowland

[57] ABSTRACT

Methods and compositions are provided for producing monoclonal antibodies capable of distinguishing between antigenic aggregates, which are differentiated by one or a small number of antigenic determinants. The method involves immunization of a mammal to produce spleen cells which are fused with a cell line which is stable in vitro. The hybridized cells are then dispensed into culture wells at a density level which encourages the production of one colony per well. Autologous antigenic aggregates are employed for screening to distinguish the antibodies which discriminate between the antigenic aggregates. Particularly, mice are hyperimmunized with a homogeneous population of T-cells, the immunized mice killed and the spleens removed. The spleen cells are fused with mouse myeloma cells and the resulting hybrids plated at a relatively low density in culture wells. Plates containing fewer than 30% hybrid positive wells are found to have primarily one colony per well. The cell supernatants are screened against autologous T- and B-cells and hybrid antibodies which do not bind to the B-cells are specific for T-cells.

1 Claim, No Drawings

MONOCLONAL ANTIBODY METHODS AND COMPOSITIONS SPECIFIC FOR SINGLE ANTIGENS IN ANTIGEN AGGREGATES

The invention described herein was made in the course of, or under, a contract from the National Institutes of Health.

CROSS-REFERENCE TO RELATED APPLICATIONS

This is a continuation of application Ser. No. 97,777, filed Nov. 27, 1979, now abandoned.

BACKGROUND OF THE INVENTION

1. Field of the Invention

With the seminal discovery by Köhler and Milstein that one could fuse a spleen cell from an immunized mouse with an appropriate myeloma cell and the resulting hybrid cell would produce monoclonal antibody in vitro, it became feasible to prepare antibodies which had high specificity for a particular spatial and polar organization. The original work was concerned with obtaining a homogeneous antibody population which recognized an antigen peculiar to a particular cell, namely a sheep red blood cell.

The ability to develop antibodies for specific antigens offered opportunities to develop antibody compositions which might be used in analytical and therapeutic ways. One area of interest is the cell surface membrane, which contains a mixture of antigenic materials. Among the potential antigenic materials are histocompatability antigens, polysaccharides, as well as other membrane proteins.

In a number of situations, one may wish to distinguish between two cells, which for the most part have the same antigenicity, but differ as to one or more antigenic determinants. Illustrative of these types of cells are T-cells and B-cells, which come from the same stem cell. The cells have different properties and functions depending upon whether they are processed by the thymus or bursa equivalent. Other situations where cells may differ in minor but extremely significant ways are cancer cells from normal cells, alloantigenic differences, or the like. It would therefore be desirable to have a method for preparing antibodies which would specifically distinguish between related cells or other aggregates of antigens, so as to permit determination of the aggregation having the antigenic site(s) of interest.

2. Brief Description of the Prior Art

Specific antigens on human T-lymphocytes have been detected using heteroantisera raised against T-lymphocytes or human thymus cells, but only after repeated absorptions with non-T-cells. Smith et al. J. Immunol. 110, 884–887 (1973); Williams et al. J. Clin. Invest. 52 283–295 (1973) and Bobrobe et al., J. Immunol. 112, 520–527 (1974). Köhler and Milstein disclosed ways for producing hybrid cell lines secreting monoclonal antibodies of defined specificity (Nature, 256 495–497 (1975) to human polymorphic antigens, such as blood group A and HLA-A2. See also, Barnstable et al. Cell, 14, 9–20 (1978) and Parham and Bodmer, Nature 276, 397–399 (1978).

SUMMARY OF THE INVENTION

Methods and compositions are provided for producing cell lines secreting an antibody which differentiates between two similar antigenic aggregates differing by one or a few antigenic determinants. The method employs fusing myeloma cells grown in vitro with cells from an animal which has been hyperimmunized with the antigenic aggregate of interest; dispensing the hybrid cells into culture wells at a sufficiently low density to encourage the formation of a single colony in a well; screening the resulting colonies with the antigenic aggregate of interest and a related antigenic aggregate differing from the antigenic aggregate of interest by only a few determinants; and isolating the colonies which produce antibodies which do not bind to the related aggregate, but bind to the aggregate of interest. The method has been specifically applied for distinguishing between T-lymphocytes and B-lymphocytes.

DESCRIPTION OF THE SPECIFIC EMBODIMENTS

The subject method and compositions are concerned with the production and use of monoclonal antibodies, a homogeneous antibody population produced by a single cell colony. These monoclonal antibodies are capable of distinguishing between two antigenic aggregates which differ by only one or a few antigenic determinants. The subject invention is concerned with the equivalence of finding a needle in a haystack, since normally the antigenic aggregates are cells which have a plurality of proteins in the membrane exposing a wide variety of antigenic sites. The subject invention is particularly applicable where one is concerned with the production of a single or a few colonies producing homogeneous antibodies which must be differentiated and isolated from an extremely large number of antibody producing colonies not of interest. There are a number of situations, where cells differ by only a few antigens or antigenic determinants and it would be of interest to be able to detect the presence of a particular type of cell in a mixture of different cell types.

One illustration of this situation is with T-lymphocytes and B-lymphocytes. These two cells fulfill different functions, the B-cell provides antibodies and the T-cell provides cell mediated immunity, graft rejection and delayed type hypersensitivity.

Another situation where cells have limited antigenic differences are tumor cells (leukemia cells, sarcoma cells, lymphomas, or the like) as compared to normal cells.

A third illustration would be allotypic cells from different sources of the same species, whose polymorphic differences can allow the production of homogeneous antibodies which will be specific for a particular individual of a species.

Because of the small number of genes associated with the antibodies of interest as compared to the total chromosomal material involved with the production of antibodies, the subject method provides for a high efficiency in the detection and isolation of the cell colony producing an antibody of interest.

In the subject invention the term "antigenic isoaggregates" will be used for at least two large aggregations of antigenic determinants, such as cells, where the aggregations differ by only a small proportion of the total determinant sites, frequently by the determinants involving a single protein or portion of a protein.

In accordance with the subject invention, a mammal, conveniently a mouse or other small mammal is hyperimmunized with a substantially homogeneous population of antigenic aggregations, for example, T-cells. Methods of immunization are well known and are amply described in the literature. The antigenic material is injected with or without adjuvants into the mammal, followed by repeated injections over relatively short periods of time. To insure the hyperimmunization of the animal, two to six subsequent booster injections will be administered. The animals are then killed, usually a few days after the last injection, the spleens removed, and the spleen cells fused with an appropriate myeloma cell line.

The manner of fusion is not a critical portion of this invention and various techniques may be employed. A common technique used today utilizes nonionic detergent; e.g. polyethylene glycol. The two cell populations are combined in the presence of the nonionic detergent, conveniently PEG 1500 and other additives, for example, Dulbecco's modified Eagle's medium, for approximately 4 minutes. The excess nonionic detergent is then rapidly removed by washing the cells.

The cells are promptly dispensed into small culture wells at a relatively low density, ranging from about $1 \times 10^5$/well to about $5 \times 10^5$/well in an appropriate medium, commonly, selective HAT medium. In this way, a major number of the wells are hybrid negative and a minor proportion hybrid positive.

After a sufficient period, usually one to two weeks, colonies of hybrids are observed and plates containing about 30% hybrid positive wells are identified. In these plates, normally not more than one colony per well is observed indicating the presence of monoclonal cultures in each positive well. In this way, one greatly enhances the ability to detect a colony producing a desired antibody. When more than one colony is found in a well, the likelihood is that one of the two colonies will be producing an undesired antibody, so that in screening the colony, the colony producing the desired antibody may go undetected.

Supernatants of each of the cultures are tested for binding activity against the immunizing antigenic aggregate, as well as the related antigenic aggregate, the antigenic isoaggregate. By employing two antigenic aggregates, for example cells having limited antigenic differences, as targets, one can rapidly screen for the discriminating antibodies. Once one has detected the colony producing the discriminating antibodies, this colony may be perpetuated to provide a continued source of the desired antibodies. The cells may be cultured in tissue culture flasks or introduced into the peritoneal cavity of a mammal.

Depending upon the particular antigenic aggregation, the antibodies can be used in a wide variety of ways. Obviously, they can be used for detecting the presence of the aggregate of interest in the presence of the antigenic isoaggregate. In addition, one can employ the antibodies for separating the aggregates, using various techniques, such as a fluorescence activated cell sorter. By conjugating the antibodies with an appropriate fluorescer, particularly one that fluoresces above 350 nm, the ligand bound to fluorescent antibodies could be segregated. In cases of cells with limited genetic differences, one would be able to characterize the existence of such modified cells, for example tumor cells, such as lymphomas and leukemias. In addition, antibodies with appropriate specificity can be employed to prevent rejection of organ transplants.

In accordance with the subject invention, female BALB/c mice were hyperimmunized with the human 8402 cell line, a homogenous population of human leukemia T-cells (Royston et al., Transpla. Proc. 7 (Suppl. 1), 531–536 (1975)). The mice were initially primed intraperitoneally (IP) with $1 \times 10^7$ cells and boosted IP at 10–14 day intervals, up to 2 to 4 times. The last injection was intravenous. Three days after the final injection of cells, the immunized mice were killed, their spleens removed and the spleen homogenized into a single cell suspension. The spleen cells ($10^8$) were mixed with $2.5 \times 10^7$ cells of the 8-azaguanine resistant myeloma cell line P3-NS1/1-Ag4-1 (Köhler and Milstein, supra; Köhler et al., Eur. J. Immun. 6, 292–295 (1976); and Galfre et al., Nature, 266, 550–552 (1977) which cannot grow in medium containing HAT (hypoxanthine, aminopterin, and thymidine) Littlefield, Science, 145 709 (1964)). To this mixture polyethylene glycol 1500 (35% V/V) was added to fuse the spleen cells with the myeloma cells. After the fusion the polyethylene glycol was diluted, the cells washed and then resuspended in Dulbecco's modified Eagles medium containing 10% fetal calf serum and HAT. The cells were dispensed into individual 0.4 ml culture wells of a 96 well Costar plate at a density ranging from $1 \times 10^5$ cells/well to $5 \times 5$ cells/well. The plates were incubated at 37° C. in a humid atmosphere containing 10% $CO_2$.

After ten days, visible colonies of hybrids were observed and plates containing fewer than 30% hybrid positive wells were identified (usually from plates receiving $2.5 \times 10^5$ cells/well). Normally, there was only one colony per well in these plates. Supernatants of these cultures were screened for binding activity against the immunizing T-cell line 8402 and the autologous B-cell line 8392 derived from the same leukemic individual (Huang et al., J. Natl. Cancr. Inst. 53 655 (1974)). Of a total of 478 different supernatants which were screened, 265 bound both T and B-cells, whereas three fluids were positive against the T-cells but not the B-cells. Only one culture (designated T101) of the three producing discriminating antibodies could be established as a cell line and its product analyzed. Cloning the cell line by limiting dilution in multiwell plates yielded 16 clones, all of which produced antibodies reactive against the T-cells but not the B-cells. The T101 culture has been deposited with the ATCC and has designation CRL-8023, deposited on Nov. 27, 1979.

The T101 supernatant was characterized by Ouchterlony immunodiffusion, immunoelectrophoresis, and polyacrylamide gel isoelectric focusing and found to contain a monoclonal murine $IgG_{2A}k$ immunoglobulin with a concentration of 20 µg/ml (by radial immunodiffusion). T101 antibody was titrated and found to have a 50% binding titer of 1/1000 against the T-cell line and no reactivity against the B-cell line.

T101 antibody was tested agains a variety of cultured and uncultured human cells. T101 antibody reacted with fetal thymus, normal peripheral blood lymphocytes, several T-cell lines and normal T-cell cultures dependent upon phytohemagglutinin conditioned medium for growth. The T101 antibody did not react with several B-cell lines, a B-cell lymphoma cell line, a myelocytic leukemia line, erythrocytes granulocytes and acute monocytic leukemia. T101 antibody also reacted with acute T-cell leukemia and T-cell lymphoma.

The binding of T101 antibody to lymphocyte subpopulations was studied using a double label immunofluorescence technique. Following incubation of cells with T101 antibody, a mixture of fluorescein-labelled F(ab')$_2$ anti-mouse IgG and rhodamine-labelled F(ab')$_2$ anti-human immunoglobulin was added, the latter to stain the surface immunoglobulin-positive B-cells. The staining with T101 antibody resulted in bright yellow-green fluorescence of all T-cell populations. The anti-mouse IgG did not react with any cells in the absence of T101 antibody. T101antibody did stain any B-cells from normal peripheral blood, lymph node, B-cell lines, granulocytes, or latex-positive monocytes. The percentage of peripheral blood mononuclear cells (substantially monocyte depleted) staining with T101 antibody was 68±13% (mean±S.D.) and was somewhat greater than the number detected by the spontaneous sheep red blood cell rosette test (E-rosette) for T-cells, which was 64±11%.

| | B AND T-LYMPHOCYTE MARKERS BY DOUBLE LABEL IMMUNOFLUORESCENCE | | | | |
|---|---|---|---|---|---|
| | SURFACE MARKERS* | | | | |
| | SURFACE | | | DOUBLE | E |
| SUBJECT | SOURCE † | Ig | HTLA | STAINING | ROSETTES |
| 9 NORMAL DONORS | PBL | 13 ± 5 | 68 ± 13 | 0 | 64 ± 11 |
| SM | LYMPH NODE NON-HODGKIN'S LYMPHOMA | 99 | 1 | 0 | ND |
| 8402 | T-CELL LINE | 0 | 100 | 0 | 5 |
| 8392 | B-CELL LINE | 100 | 0 | 0 | 0 |

*Numbers represent percentage of cells positive for each marker. A minimum of 200 cells were counted. ND, not done. HTLA, human T-lymphocyte antigen detected by T101 antibody. For the E rosette test, T cells were counted by the formation of rosettes with sheep erythrocytes, as described.

Peripheral blood lymphocytes (PBL), separated by Ficoll-hypaque sedimentation, were incubated for 24 hrs. in medium containing 10% fetal calf serum (FCS) in a plastic flask. The majority of the monocytes were removed by plastic adherence. Those not removed did not stain with T101 antibody. The lymph node was mechanically minced into a single cell suspension and the cells incubated for 24 hrs. in medium containing 10% FCS.

For simultaneous examination of T and B-cells, viable cells were first incubated with T101 antibody or medium for 30 min. at 4° C., washed, and stained for 30 min. at 4° C. with a mixture of ±luorescein-labelled goat F(ab')2 anti-human immunoglobulin. The cells were washed, smeared on a glass slide, fixed in 100% ethanol. mounted with a cover slip, and examined under a fluorescence microscope. The surface Ig positive B-cells displayed bright red membrane fluorescence.

The human T-lymphocyte antigen detected by T101 antibody is designated HTLA. T101 hybridomas were passaged in pristane primed mice. The ascites fluids collected from these mice had 50% binding titers of approximately 1/50,000 against T-cells.

The observed results confirm the presence of a unique T-cell antigen in humans and the ability of xenogeneic monoclonal antibodies to recognize differences between surface antigens on human lymphocyte subpopulations. Furthermore, the technique demonstrates the feasibility of growing monoclonal hybridomas immediately after cel fusion by limiting dilution plating of the fused cells and has further demonstrated the usefulness of detecting xenogenic monoclonal antibodies of defined specificity by screening them against target cells with limited antigenic differences.

The subject monoclonal anti-HTLA antibody is unique in its ability to react with all thymic derived lymphocytes, including mature T-cells, thymus cells, activated T-cells, T-cell lines, and malignant T-cells.

The subject monoclonal anti-HTLA antibody can be employed for enumerating human T-lymphocytes in the peripheral blood of patients, as well as for purification and immuno-chemical analysis of the HTLA molecule. The antibody may be used for the removal of T-lymphocytes from lymphoid populations. In addition, the antibody can be employed for characterizing functional human lymphocyte subpopulations and for classification of human malignant lymphomas and leukemias. Furthermore, T-cell antibodies may find application in the treatment of organ rejection in allograft recipients, graft versus host disease, and T-cell neoplasms.

The subject monoclonal antibodies are particularly useful in defining the antigenic aggregate of interest, when found in a mixture of similar antigenic aggregates.

A vast array of assays are predicated on the use of antibodies capable of differentiating between similar compounds or compositions. In certain assays, the ligand is labeled with a radiocarbon label, an enzyme or a fluorescer. In other assays, the antibody may be labeled with a fluorescer, a quencher, and enzyme or the like. See, for example, U.S. Pat. Nos. 3,996,345; and 4,016,043.

In accordance with the subject invention a novel efficient method is provided for obtaining monoclonal antibodies and monoclonal cells secreting antibodies specific for a particular determinant site. The method overcomes the significant problem associated with the vast quantity of antigenic determinants which are present on cells and other antigenic aggregations. The method finds particular application in providing monoclonal antibodies which can distinguish between antigenic aggregates which differ by only one or a few determinants, such as autologous cells, T- and B-cells and the like.

Although the foregoing invention has been described in some detail by way of illustration and example for purposes of clarity of understanding, it will be obvious that certain changes and modifications may be practiced within the scope of the appended claims.

What is claimed is:

1. Antibodies produced by hybridoma cells having A.T.C.C. accession number CRL-8023 and capable of binding with all thymic derived lymphocytes and distinguishing such lymphocytes from B-cells.

* * * * *